United States Patent [19]
Grimard et al.

[11] Patent Number: 5,865,798
[45] Date of Patent: *Feb. 2, 1999

[54] STOPPER ASSEMBLY HAVING BYPASS FEATURES FOR USE IN A MULTI-CHAMBER SYRINGE BARREL

[75] Inventors: Jean Pierre Grimard, Vif; Hubert Jansen, Haute Jarrie, both of France

[73] Assignee: Becton Dickinson France, S.A., Le Pont de Claix, France

[*] Notice: This patent issued on a continued prosecution application filed under 37 CFR 1.53(d), and is subject to the twenty year patent term provisions of 35 U.S.C. 154(a)(2).

[21] Appl. No.: 672,788

[22] Filed: Jun. 28, 1996

[51] Int. Cl.$^6$ .................................................. A61M 37/00
[52] U.S. Cl. ............................................ 604/89; 604/218
[58] Field of Search ............................... 604/89–91, 191, 604/218, 187, 221, 82, 49–51

[56] References Cited

U.S. PATENT DOCUMENTS

| | | |
|---|---|---|
| 3,331,538 | 7/1967 | Higgins . |
| 3,957,051 | 5/1976 | Topham ............................. 604/218 X |
| 4,465,476 | 8/1984 | Gahwiler ................................. 604/191 |
| 4,599,082 | 7/1986 | Grimard . |
| 4,929,230 | 5/1990 | Pfleger . |
| 5,489,266 | 2/1996 | Grimard .................................... 604/89 |
| 5,599,312 | 2/1997 | Higashikawa . |
| 5,704,918 | 1/1998 | Higashikawa . |

FOREIGN PATENT DOCUMENTS

| | | |
|---|---|---|
| 0 172 990 A1 | 3/1986 | European Pat. Off. . |
| 0 664 137 A2 | 7/1995 | European Pat. Off. . |
| 0 695 555 A1 | 2/1996 | European Pat. Off. . |
| WO 95/09020 | 9/1994 | WIPO . |

Primary Examiner—John D. Yasko
Attorney, Agent, or Firm—Allen W. Wark

[57] ABSTRACT

A stopper assembly having by-pass features for use in a multi-chamber syringe barrel. The stopper assembly includes a sequential stopper body responsive to fluid forces for enabling the sequential delivery of disparate contents, such as disparate fluids, separately held in the syringe barrel. The sequential stopper body has a generally cylindrical sidewall with a distal end, a proximal end and a longitudinal axis therethrough. The stopper assembly also includes a generally cylindrical flow channelizer mounted to the distal end of the sequential stopper body. The flow channelizer enables the reconstitution of dry medicament held in the syringe barrel distally of the flow channelizer. The flow channelizer features opposed proximal and distal ends and a generally cylindrical outer surface therebetween. At least one fluid flow channel extends between the proximal and distal ends of a flow channelizer. A distally directed, conically-shaped projection is located at the distal end of the flow channelizer to prevent the accumulation of dead space between the channelizer and the internal shoulder located at the distal end of the syringe barrel. The stopper assembly may be employed in a multi-chambered syringe barrel featuring a by-pass channel to permit fluids to pass distally of the stopper assembly. The multi-barreled syringe barrel can be separated into disparate chambers by one or more by-pass stoppers so as to contain disparate components intended for sequential delivery by the stopper assembly.

21 Claims, 9 Drawing Sheets

STOPPER ASSEMBLY HAVING BYPASS FEATURES FOR USE IN A MULTI-CHAMBER SYRINGE BARREL

I. FIELD OF THE INVENTION

The invention relates to stoppers, and more particularly, to a stopper assembly having bypass features to promote reconstitution of a dry drug, such as a lyophilized drug, held in a hypodermic syringe barrel and then to promote complete sequential injection of disparate contents held in separate chambers in the syringe barrel.

II. BACKGROUND

As is known in the art, hypodermic syringes include an elongate barrel having opposed proximal and distal ends with a chamber therebetween for receiving a fluid. A passageway extends through the distal end of the syringe barrel and communicates with the chamber. The distal end of the syringe barrel is connected to a piercing element, such as a needle cannula or a blunt cannula, for delivering fluid from the chamber and passageway. The proximal end of the syringe barrel receives a plunger rod and stopper assembly. Force applied to the plunger rod urges the stopper along the barrel to drive liquid from the chamber through the needle cannula.

Oftentimes, it is desired to deliver from the hypodermic syringe a number of discrete substances held within the chamber. These discrete substances normally must be held separate from one another until such time as delivery to the patient is desired. It is necessary, then, that the chamber defined between the proximal and distal ends of the elongate barrel be divided into a discrete number of chambers, each capable of holding a substance intended for delivery to a patient.

Bearing the foregoing in mind, it would be useful to construct a hypodermic syringe capable of simultaneously storing a medicament together with any components which are to be administered, with the ability to keep the medicament and the components separate until administration is desired. Medicaments storable in hypodermic syringes can be in liquid form or in dry form. It is often desirable to store medicaments in dry form since, depending on the type of medicament, it will display a longer shelf-life vis-a-vis the liquid form of the drug. As the skilled artisan will appreciate, one way to reduce a liquid drug to dry form is through a lyophilization process. In this process, liquid medicaments are subjected to a freeze-drying, or lyophilization, process, that reduces the liquid medicament to a dried powder or granular form. For purposes of simplicity, reference in this patent application to a drug in lyophilized form is intended to encompass any dry medicament, all of which require reconstitution prior to delivery.

Frequently, dry medicaments are located in a multi-chamber syringe barrel in the chamber located most adjacent the piercing element. In order to administer the medicament to a patient, a diluent is introduced into the chamber containing the dry medicament in order to reconstitute the drug into its liquid form. Thereafter, the reconstituted medicament can be administered from the same multi-chamber syringe which had stored the lyophilized medicament. It is also desirable to isolate the dry medicament from the ambient environment until such time as reconstitution and delivery is desired.

With the foregoing objectives in mind, U.S. Pat. No. 4,929,230 to Frederick W. Pfleger ("Pfleger '230"), whose disclosure is specifically incorporated by reference herein, describes a particular stopper construction useful for dividing the syringe barrel into a plurality of chambers and allowing separate liquid contents held by the syringe barrel to be sequentially administered to a patient. Making particular numerical reference to components disclosed by Pfleger '230, there is disclosed a free piston (or stopper) 33 including a hollowed chamber 48 facing the end wall 23 of the syringe barrel. Chamber 48 can be realized as a hollow circularly disposed about the central axis of stopper 33 (FIGS. 5, 6, 7) or, as shown in FIGS. 9, 10 or 11, it can assume a flattened, narrow configuration offset from the central axis of the stopper. Stopper 33 includes a closed end 34, which faces away from end wall 23 of the syringe barrel. Closed end 34 has a diameter less than the interior diameter of the syringe barrel. A peripheral sidewall 35 obliquely extends between closed end 34 of stopper 33 and a cylindrical peripheral sealing surface 36 in contact with the interior surface of the syringe barrel. Oblique sidewall 35 overlaps with a portion of hollowed chamber 48. It is stated at Col. 3, lines 15–17, that the oblique sidewall 35 has its large end generally cylindrical, as the sealing surface 36, for sealing engagement with the syringe barrel, and it is stated at Col. 3, lines 19–23, that external ribs 37 help prevent tipping of the piston as it moves in the syringe barrel. It is believed by the inventors herein that the oblique sidewall 35 is itself cylindrically formed around stopper 33 and, thus, extends about the entire circumference of the stopper. A force is generated by a proximal-most stopper 31 connected to plunger rod 30, stopper 33 will come to rest adjacent internal shoulder 25 of the syringe barrel. Continued motion by stopper 31 increases the fluid forces exerted upon oblique sidewall 35 to overcome the resilient material sealing forces inherent in stopper 33. Because of the presence of hollowed chamber 48, oblique sidewall 35 will collapse inwardly, allowing the fluid contents held proximally of closed end 34 to proceed in a distal direction for delivery through the needle cannula.

Pfleger '230 is not particularly suited to an application requiring the reconstitution of a dry drug before the sequential delivery of other components, such as flushes, retained by the syringe barrel. For instance, neither the teaching of Pfleger '230, nor the structure of Pfleger '230, is adapted to permit reconstitution of a medicament held in dry form in a chamber of the syringe barrel. Pfleger '230 is directed towards sequential delivery of liquid components but not to sequential delivery of a dry component.

Moreover, in certain prior art hypodermic syringes, a certain amount of liquid can remain in the syringe barrel after the stoppers are advanced the full length of the barrel during an injection process. There remains in most syringes a certain residual volume, no matter how small, which is trapped between the end of the stopper and the needle tip, which includes the volume of the needle cannula and the volume presented at the distal end of the syringe barrel. A quantity of the medication can also be trapped in the area around and between the sidewalls of the stopper and the interior of the syringe barrel. In the case of expensive medications and medications requiring extreme precision and delivery, this so-called "dead space" must be overcome by overfilling the barrel in order to ensure that the proper dose is delivered. The additional medication will be disposed of with the used syringe. The costs associated with the dead volume can accumulate substantially. It would be beneficial to prevent waste of medication trapped in the syringe barrel, for instance, as evidenced by Pfleger '230 between hollow end 48 of the stopper, internal shoulder 25 located at the extreme distal end of the syringe barrel, and outlet port 24 associated with the syringe barrel. A quantity of medication that can be held between these surfaces is seen, for instance, in FIG. 7 of Pfleger '230.

Accordingly, there is a need for a sequential stopper having bypass features to promote reconstitution of a dry drug held in a syringe barrel and which thereafter allows sequential injection of a series of disparate contents held in separate chambers in the syringe barrel, all of which results in reducing the amount of medicament trapped in the syringe barrel after delivery. Such a stopper is disclosed herein.

III. SUMMARY OF THE INVENTION

A stopper assembly in accordance with the present invention includes two components: (a) a piston-like, sequential stopper body responsive to fluid forces for enabling the sequential delivery of disparate contents, such as disparate fluids, separately held in the syringe barrel in a location proximal of the sequential stopper body; and (b) a generally cylindrical flow channelizer mounted to the distal end of the sequential stopper body to enable reconstitution of a dry medicament, such as a lyophilized medicament, held in the syringe barrel in a location distal of the flow channelizer and to thereafter enable the sequential delivery of the disparate fluids held proximally of the sequential stopper body through a fluid passage provided in the syringe barrel.

The stopper assembly in accordance with the present invention may be employed in a multi-chamber syringe barrel that is configured to retain the lyophilized medicament as well as the disparate fluids. The stopper assembly may be located adjacent the distal end of the syringe barrel in a manner so as to define a chamber located distally of the flow channelizer which contains the lyophilized medicament. One or more bypass stoppers may be located proximally of the sequential stopper body in a manner to divide the syringe barrel into separate chambers for holding the disparate fluids separate from one another. A bypass channel is provided in the wall of the syringe barrel to permit the disparate fluids to pass sequentially between their respective chambers and through fluid flow channels defined on the flow channelizer for delivery through the passage of the syringe barrel.

The sequential stopper body has a generally cylindrical sidewall with a distal end, a proximal end, and a longitudinal axis therethrough. An elongate hollow chamber is disposed within the interior of the sequential stopper body. Preferably, the elongate hollow chamber is disposed to one side of the longitudinal axis of the sequential stopper body. The elongate hollow chamber includes a distal end, a proximal end, and may include an opening communicating with the distal end of the sequential stopper body. One or more sealing elements are circumferentially disposed about the sidewall of the sequential stopper body. The circumferential sealing elements can be formed as a plurality of rings circumferentially formed about the piston-like sequential stopper body.

The stopper assembly of the present invention includes structure designed to reconstitute a lyophilized medicine and to direct substantially all of the fluids held proximally of the stopper assembly in a distal direction for substantially complete delivery to a piercing element affixed to the distal end of the syringe barrel. To this end, a pair of sealing elements are longitudinally disposed along the sidewall of the sequential stopper body in preferably parallel relation to the longitudinal axis. The pair of longitudinal sealing elements are each located along the sidewall and separated by a distance at least equal to if not slightly greater than the maximum width defined by the elongate hollow chamber formed within the sequential stopper body.

In a preferred embodiment, the cylindrical sidewall and/or the circumferential sealing elements of the sequential stopper body are largely in fluid-tight contact with the interior surface of the syringe barrel. However, a portion of the cylindrical sidewall is recessed from the interior surface of the syringe barrel to provide means to exert fluid pressure onto a portion of the circumferential sidewall in order to cause only that portion of the circumferential sidewall to collapse towards the hollow chamber, thereby establishing a fluid conduit between the distal and proximal ends of the sequential stopper body. In a preferred embodiment, the recessed portion of the cylindrical sidewall is formed as a sloping surface adjacent the proximal end of the stopper body that is located between the pair of longitudinal sealing elements.

The flow channelizer includes at least one fluid flow channel extending between the proximal and distal ends of the flow channelizer. In a preferred embodiment, one or more helically oriented flow channels are provided around the flow channelizer. The fluid flow channels communicate fluid passing distally of the sequential stopper assembly to the passage of the syringe barrel. A distally directed, substantially conically-shaped projection is located on the distal end of the flow channelizer. The distally-directed, conically-shaped projection can be dimensioned to substantially conform to the shape assumed by the internal shoulder located at the distal end of the syringe barrel.

In use, fluid force exerted upon the proximal-end of the sequential stopper body causes the sequential passage of the disparate fluids that are held proximally of the sequential stopper body through the fluid channel of the syringe barrel and the flow channels of the flow channelizer. The medicament is thus reconstituted in and delivered from the chamber located distally of the flow channelizer. Continued fluid pressure on the proximal end of the sequential stopper body will eventually cause the flow channelizer to seat adjacent the distal end of the syringe barrel. The distally-directed, conically-shaped projection, conforming substantially to the shape of the internal shoulder located at the distal end of the syringe barrel, prevents excessive accumulation of fluid in that area.

Once the flow channelizer is seated against the distal end of the syringe barrel, increasing fluid force exerted on the recessed portion of the cylindrical sidewall of the sequential stopper body causes the portion of sidewall located between the longitudinal sealing elements to collapse towards the hollow chamber. The collapse of the sidewall in this area initiates a fluid conduit between the proximal and distal ends of the sequential stopper body restricted generally to that portion of the cylindrical sidewall of the sequential stopper body located between the longitudinal sealing elements to enable the sequential delivery of a second liquid held proximally of the stopper assembly. The longitudinal sealing elements themselves, together with the portion of the circumferential sealing elements not located between the longitudinal sealing elements, remain in fluid-tight contact with the syringe barrel. Accordingly, fluid is substantially prevented from accumulating around the cylindrical sidewalls of the sequential stopper body or between the distally-directed conically shaped projection and the corresponding distal end of the syringe barrel, such that fluid is substantially entirely directed through the fluid conduit for delivery through the fluid flow channels of the flow channelizer and out of piercing element attached to the distal end of the syringe barrel.

IV. BRIEF DESCRIPTION OF THE DRAWINGS

The invention will now be described in more detail by way of reference to the appended drawings, wherein.

V. DETAILED DESCRIPTION OF THE PREFERRED EMBODIMENT

A convention used in this patent application is that the term "distal" refers to an end closer to the needle end of a syringe barrel, whereas the term "proximal" refers to an end farther away from the needle end of the syringe barrel.

Turning now to the drawings, wherein like numerals denote like components, FIGS. 2–5 denote one embodiment 200 of the stopper assembly in accordance with the present invention. FIGS. 1 and 6–12 illustrate stopper assembly 200 in conjunction with a multi-chambered syringe barrel 100. FIGS. 6–12 particularly illustrate use of stopper assembly 200 in reconstituting a lyophilized medicament "M" held distally of the stopper assembly, together with the sequential delivery of disparate contents held in separate chambers defined proximally of stopper assembly 200.

For ease of explanation, particulars of stopper assembly 200 will be explained first. Thereafter, use of the stopper assembly in conjunction with the multi-chambered syringe barrel will ensue.

Turning then to FIGS. 2–5, stopper assembly 200 includes a sequential stopper body 201 and a flow channelizer 225. Sequential stopper body 201 includes a proximal end 204, a distal end 206, and a cylindrical sidewall 202 extending therebetween. The sequential stopper body is characterized by longitudinal axis 208. Likewise, flow channelizer 225 features a proximal end 226, a distal end 228, and one or more fluid flow channels 238 extending therebetween. The construction of flow channelizer 225 is analogous to that described in U.S. patent application Ser. No. 5,489,266 "Syringe Assembly and Method for Lyophilizing and Reconstituting Injectable Medication", whose disclosure is specifically incorporated by reference herein.

FIGS. 2–5 illustrate that stopper assembly 200 is formed in separate components, viz., a sequential stopper body 201 and a flow channelizer 225, that are connected cooperative mating structure. For example, a protrusion 242 can be provided from distal end 206 of the sequential stopper body that is configured for insertion into an aperture 240 that is defined on distal end 226 of the flow channelizer. The protrusion can include a groove 244 configured to mate with one or more nubs 246 defined within the aperture. Of course, it will be understood that the placement of the protrusion and aperture can be reversed between sequential stopper body 201 and flow channelizer 225, as can be the location of the groove and nubs. The resulting connection will result in secure fixation of sequential stopper body 201 to flow channelizer 225. Other cooperative structure for securing the sequential stopper body to the flow channelizer, such as by adhesively bonding, is also within the purview of the invention. Furthermore, if desired, sequential stopper body 201 and flow channelizer 225 can be configured for releasable mating contact, such as by providing a threaded interface between protrusion 242 and aperture 240. Likewise, if desired, stopper assembly 200 can be formed in a unitary manner from one component, in lieu of separating providing the sequential stopper body 201 from flow channelizer 225.

Turning now more particularly to sequential stopper body 201, a plurality of sealing elements may be provided on the sequential stopper body for sliding fluid-tight contact between the sequential stopper body and the interior surface 140 of syringe barrel 100 (see FIGS. 1 and 6–12). One or more circumferentially disposed sealing elements 210 are provided about cylindrical sidewall 202. In the embodiment depicted herein, four such of circumferential sealing elements 210a, b are provided. Here, a proximal-most circumferential sealing element 210b is located adjacent proximal end 204 of the sequential stopper body, such that fluid can be prevented from accumulating between cylindrical sidewall 202 and interior surface 140 of syringe barrel 100 in the area proximal of circumferential sealing elements 210a, themselves located intermediate the proximal and distal ends of sequential stopper body 201. It will be realized by the skilled artisan that any number of circumferential sealing elements may be chosen according to the size of the stopper or as need or desire dictate.

Figure 3:
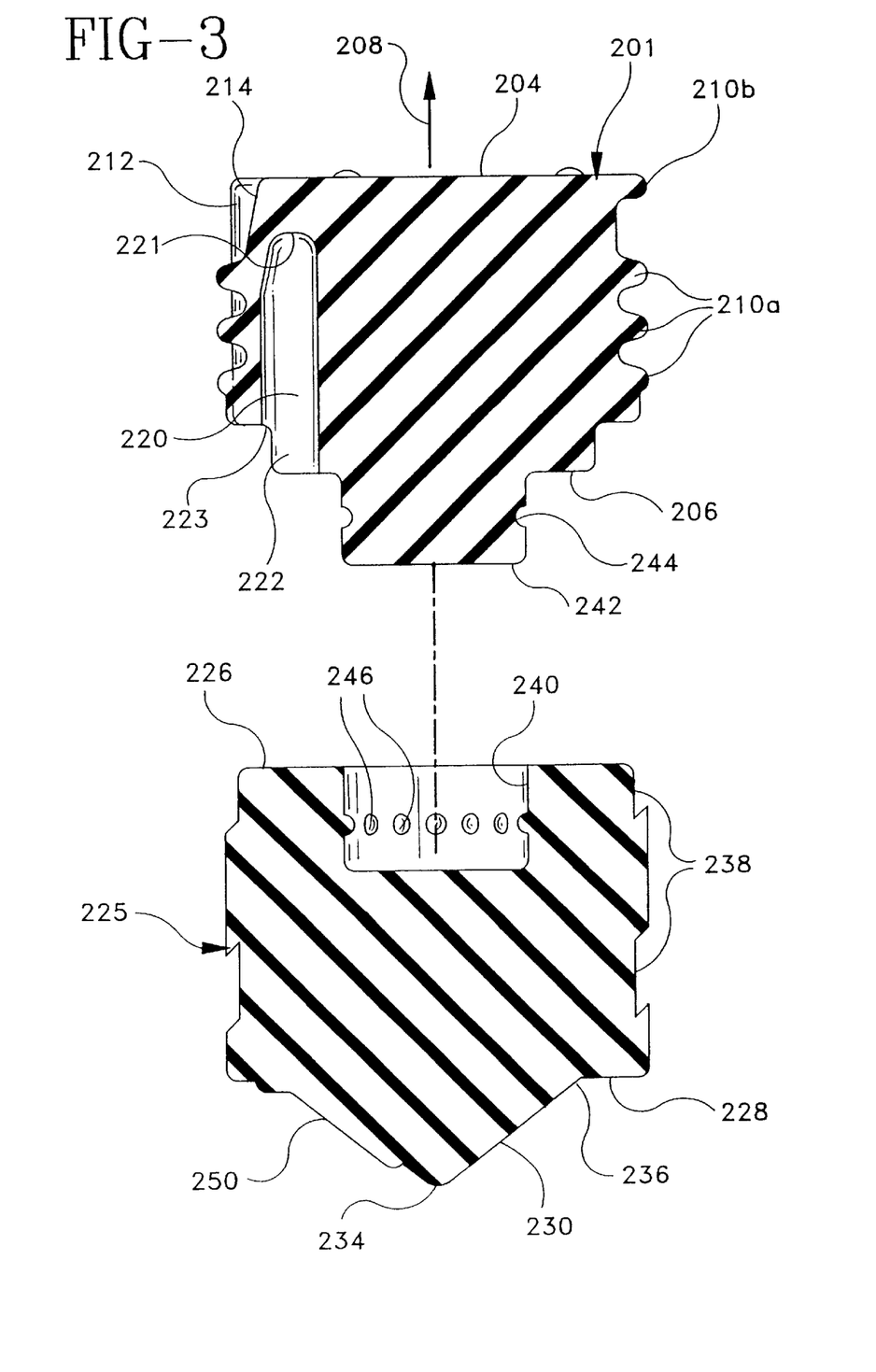
FIG. 3 is a cut-away view of the stopper assembly of the present invention, taken along line 3—3 of FIG. 2.

Sequential stopper body 201 includes an elongate hollow chamber 220 disposed in a direction which is preferably substantially parallel to longitudinal axis 208. As best seen in FIG. 3, the elongate hollow chamber 220, which can assume a flattened shape, is preferably not concentric with longitudinal axis 208 and is preferably disposed adjacent cylindrical sidewall 202. Hollow elongate chamber 220 features a proximal end 221 located within the interior of the sequential stopper body and a distal end 223. The purpose of elongate hollow chamber 220 is analogous to hollow chamber 48 of Pfleger '230, as previously discussed. As here shown, it is envisaged that owing to mold tooling conventionally employed to form sequential stopper body 100, distal end 223 of the chamber will communicate with distal end 206 of sequential stopper body 201 via an opening 222. However, it will be understood by the skilled artisan that elongate chamber 220 can be formed by other ways such that it is entirely within the sequential stopper body without an opening 222.

Figure 1:
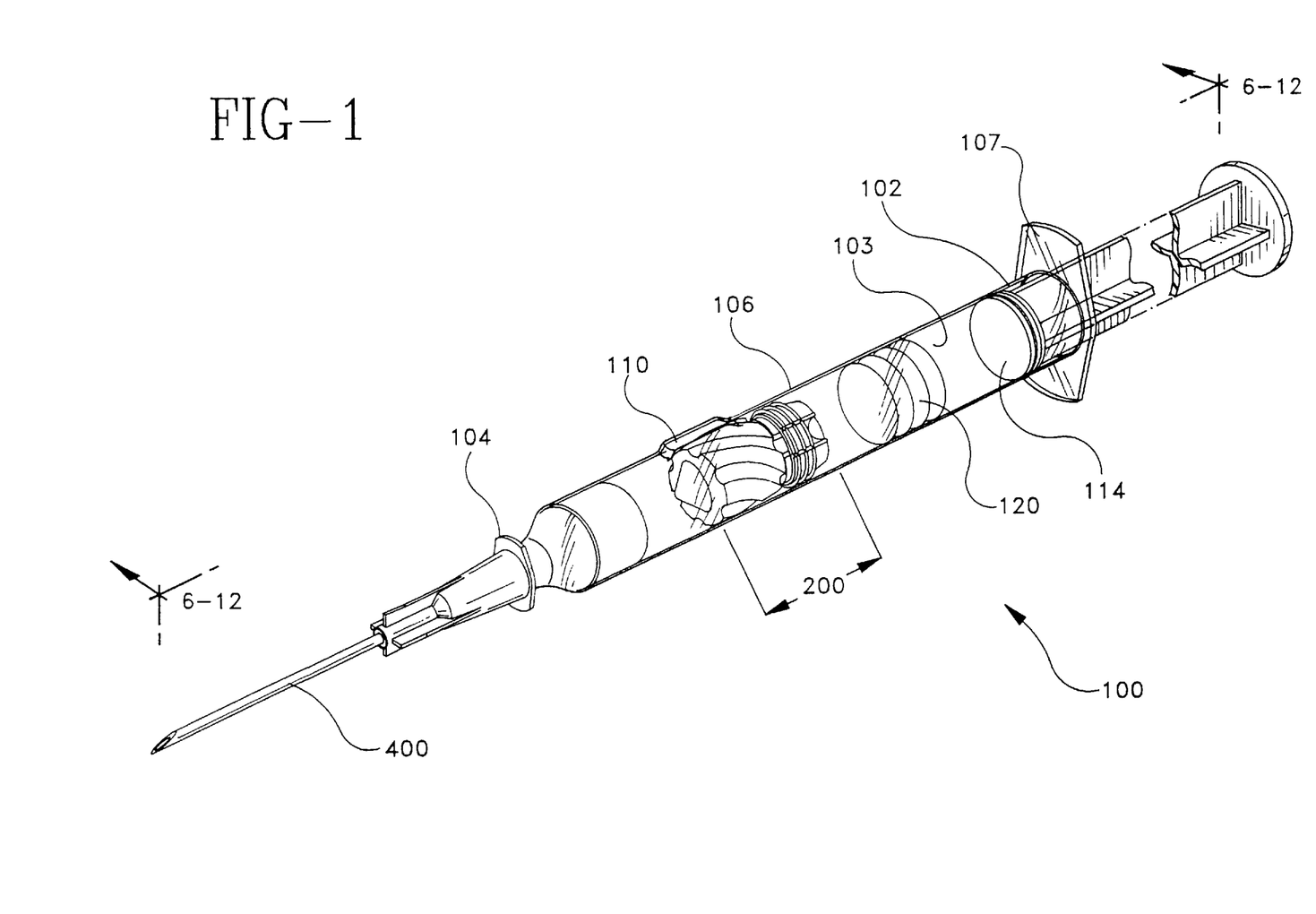
FIG. 1 is a perspective view of a syringe assembly employing the stopper assembly in accordance with the present invention.
Figure 2:
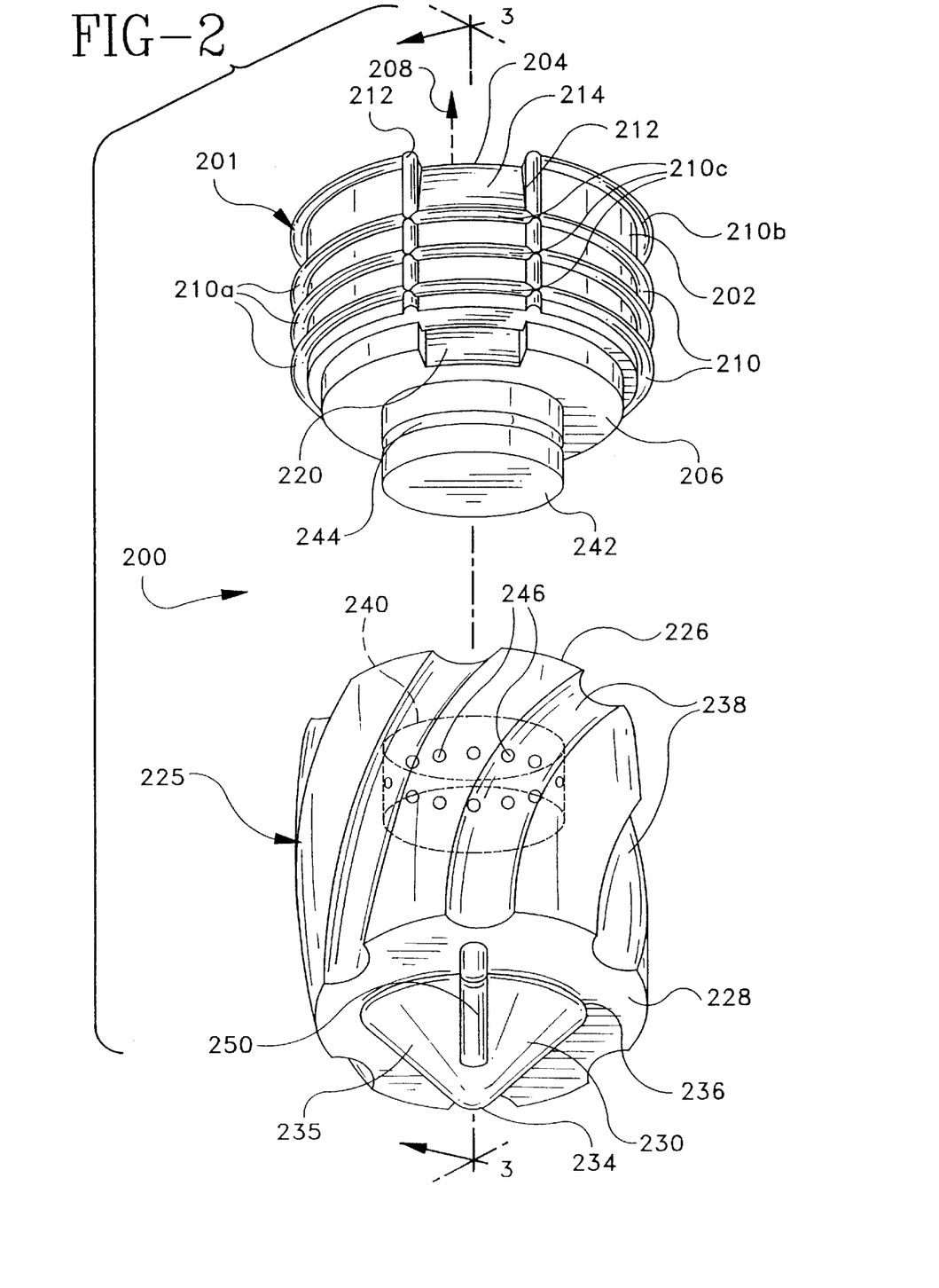
FIG. 2 is an exploded perspective view of the stopper assembly in accordance with the present invention, illustrating both the sequential stopper body and the flow channelizer.
Figure 4:
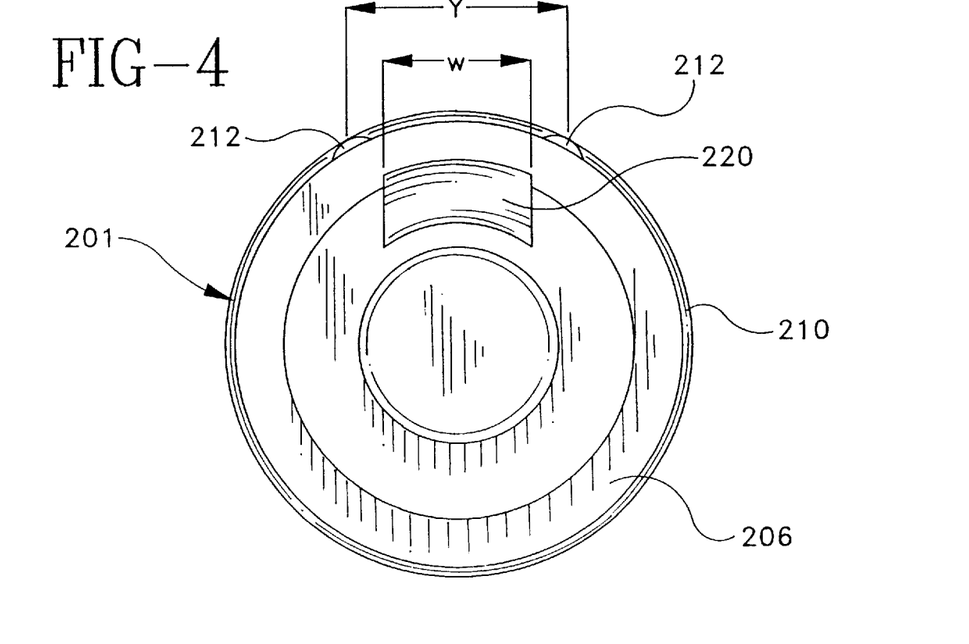
FIG. 4 is a bottom view of the sequential stopper body depicted in FIG. 2.
Figure 5:
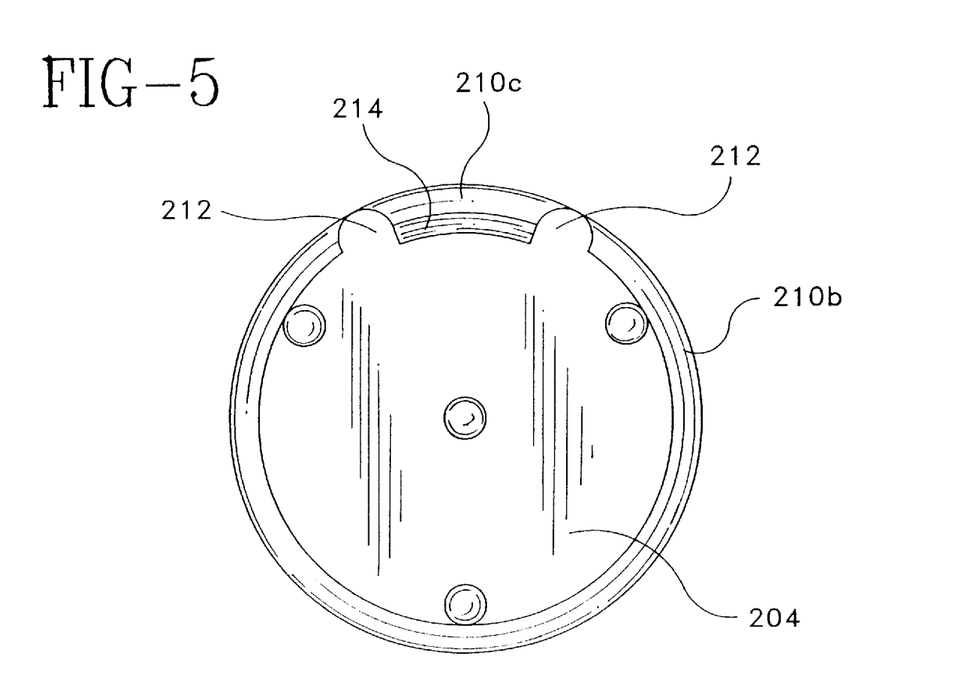
FIG. 5 is a top view of the sequential stopper body depicted in FIG. 2.

A feature of stopper assembly 200 in accordance with the present invention is that it features structure designed to minimize a quantity of medicament which would be trapped between stopper assembly 200 and syringe barrel 100, and which would be otherwise wasted when the syringe barrel were disposed of following use. To this end, sequential stopper body 201 features a pair of longitudinal sealing elements 212 preferably disposed on cylindrical sidewall 202 in substantially parallel relationship with longitudinal axis 208. As best seen in FIGS. 2, 4 and 5, longitudinal sealing elements 212 are spaced from one another on cylindrical sidewall 202 by a distance "Y" that is at least equal to, if not slightly greater than, a maximum width "W" displayed by elongate hollow chamber 220. For the purposes of this patent application, a reference to a portion or an area of cylindrical sidewall 202 that is located between longitudinal sealing elements 212 shall mean that portion or area of cylindrical sidewall 202 which is encompasses by distance "Y" separating the longitudinal sealing elements.

Figure 9:
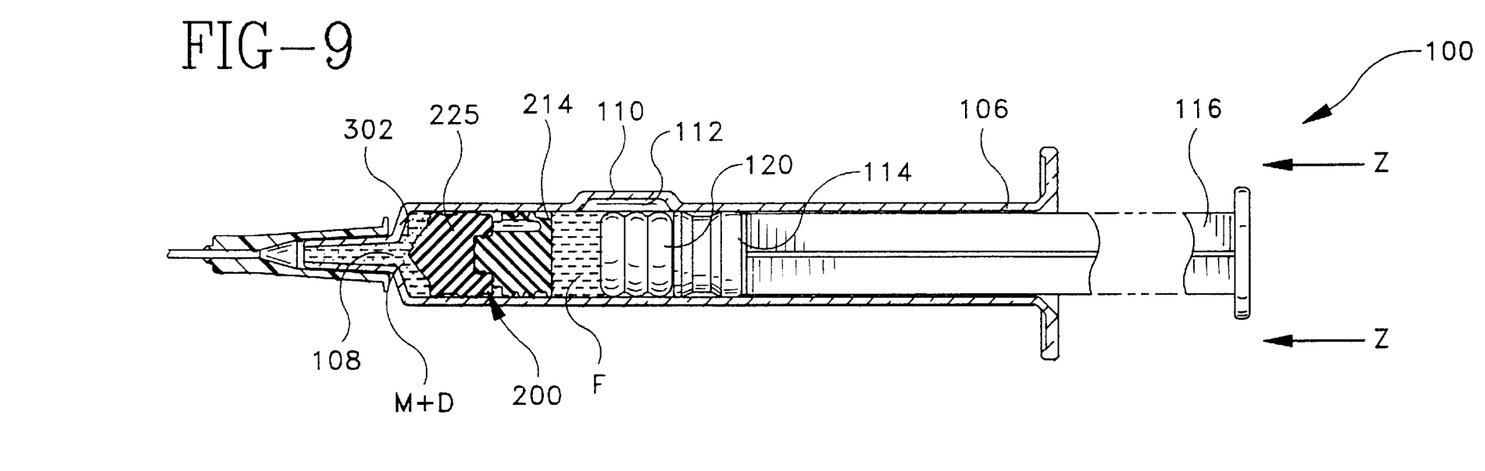
FIG. 9 is a fourth cross-sectional view of the syringe assembly of FIG. 1, illustrating the full location of the flush agent in the chamber formerly occupied by the diluent.
Figure 10:
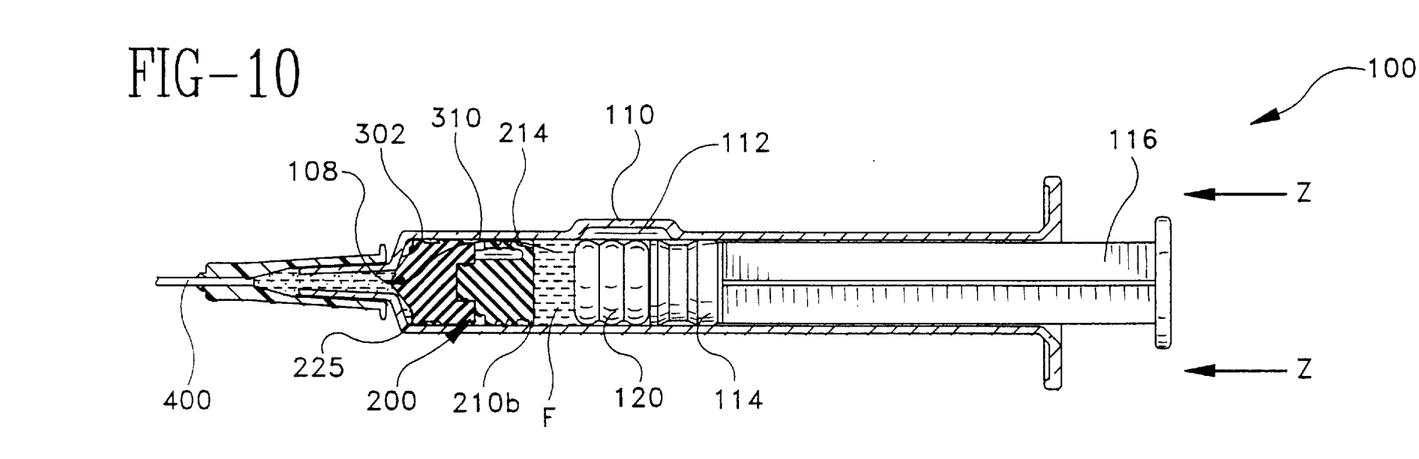
FIG. 10 is a fifth cross-sectional view of the syringe assembly of FIG. 1, illustrating full seating of the flow channelizer against the distal end of the syringe barrel and the collapse of the cylindrical sidewall of the sequential stopper body between the longitudinal sealing elements, to establish a fluid conduit between the proximal and distal ends of the sequential stopper body such that the flush agent is delivered to the fluid flow channels of the flow channelizer for delivery through the passage of the syringe.
Figure 11:
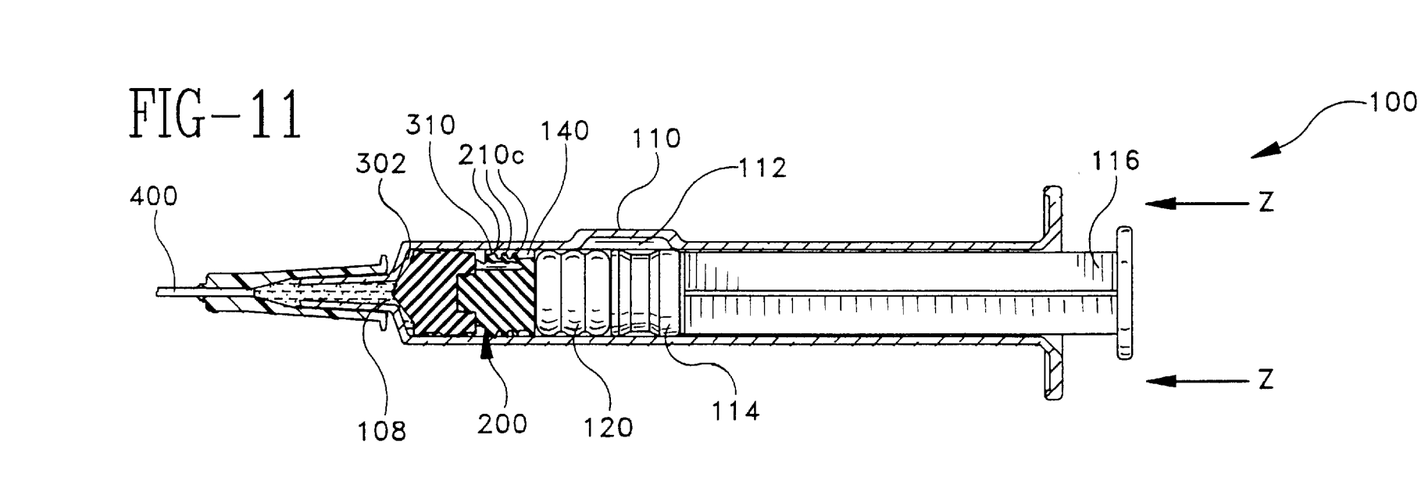
FIG. 11 is a sixth cross-sectional view of the syringe assembly of FIG. 1, illustrating the end of the injection sequence.
Figure 12:
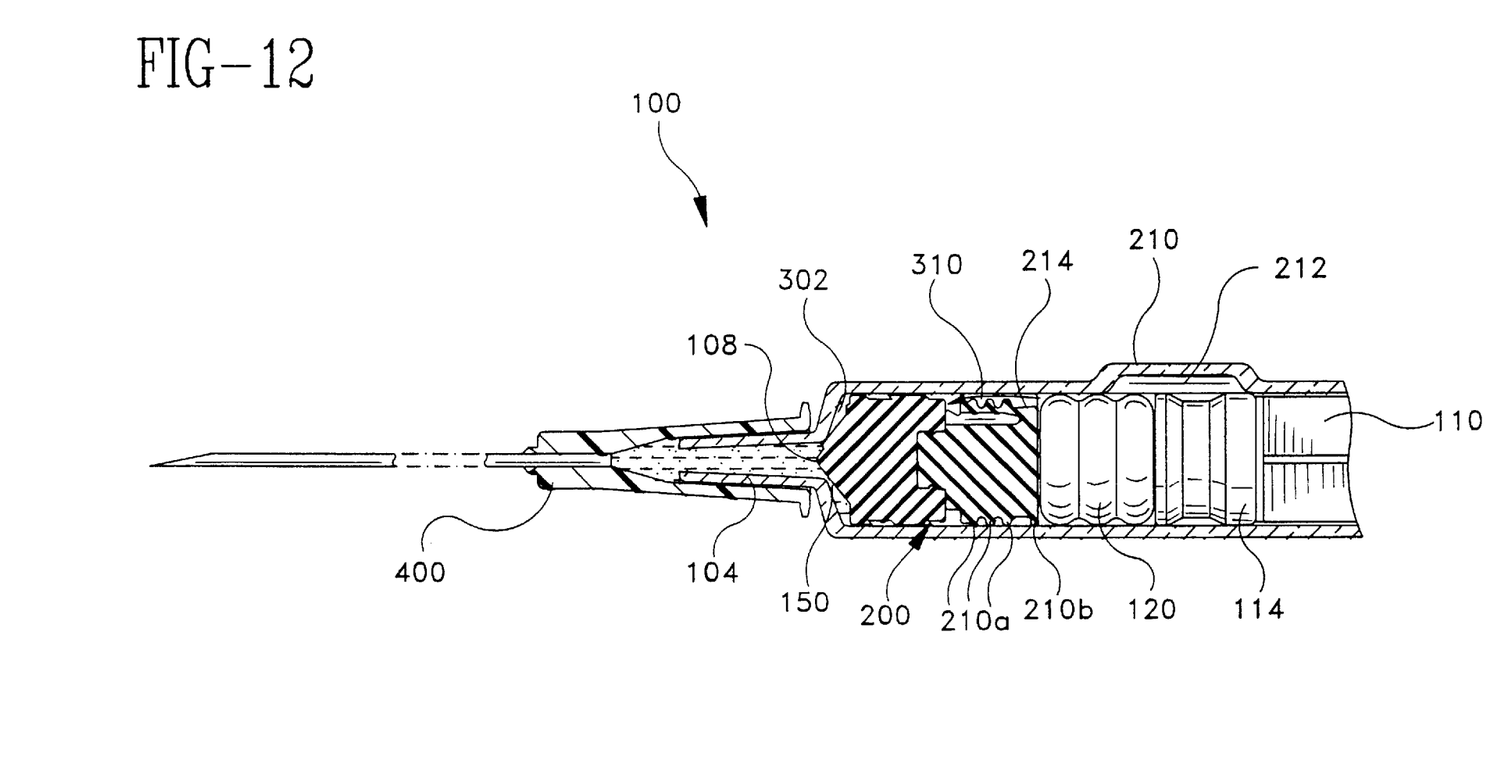
FIG. 12 is a partial cross-sectional view of the syringe assembly of FIG. 1, illustrating the placement of the various components at the end of the injection sequence.

As will be evident in ensuing discussion of the operation of stopper assembly 200 in an injection sequence (FIGS. 6–12), upon full seating of flow channelizer 225 against internal shoulder 302 of the syringe barrel, it will be required to initiate a fluid conduit between the proximal and distal ends 204, 206 of sequential stopper body 201 such that a last remaining disparate contents held proximally of stopper assembly 200 will be permitted to pass between the proximal and distal ends of the sequential stopper body and through the channels 238 of flow channelizer 225 for delivery through passage 108 of syringe 100 (see FIGS. 10–12). To this end, it is an aspect of stopper assembly 200 in accordance with the present invention to initiate a fluid conduit 310 between the proximal and distal ends of the sequential stopper body only in the area of cylindrical sidewall 202 located between longitudinal sealing elements 212. Sequential stopper body 201 is itself disposed for sliding, fluid-tight relationship with interior surface 140 of syringe barrel 100— as here depicted, by the sliding fluid-tight relationship between circumferential sealing elements 210a, b and interior surface 140 of the syringe barrel. One way to initiate fluid conduit 310 is to space a portion of cylindrical sidewall 202 that is adjacent proximal end 204 and between longitudinal sealing elements 212, such that this portion of the cylindrical sidewall is not in fluid-tight contact with interior surface 140 of the syringe barrel. In this way, fluid force can act upon the portion of cylindrical sidewall 202 located between sealing elements 212 to collapse that portion of the sidewall towards hollow chamber 220.

Figure 3A:
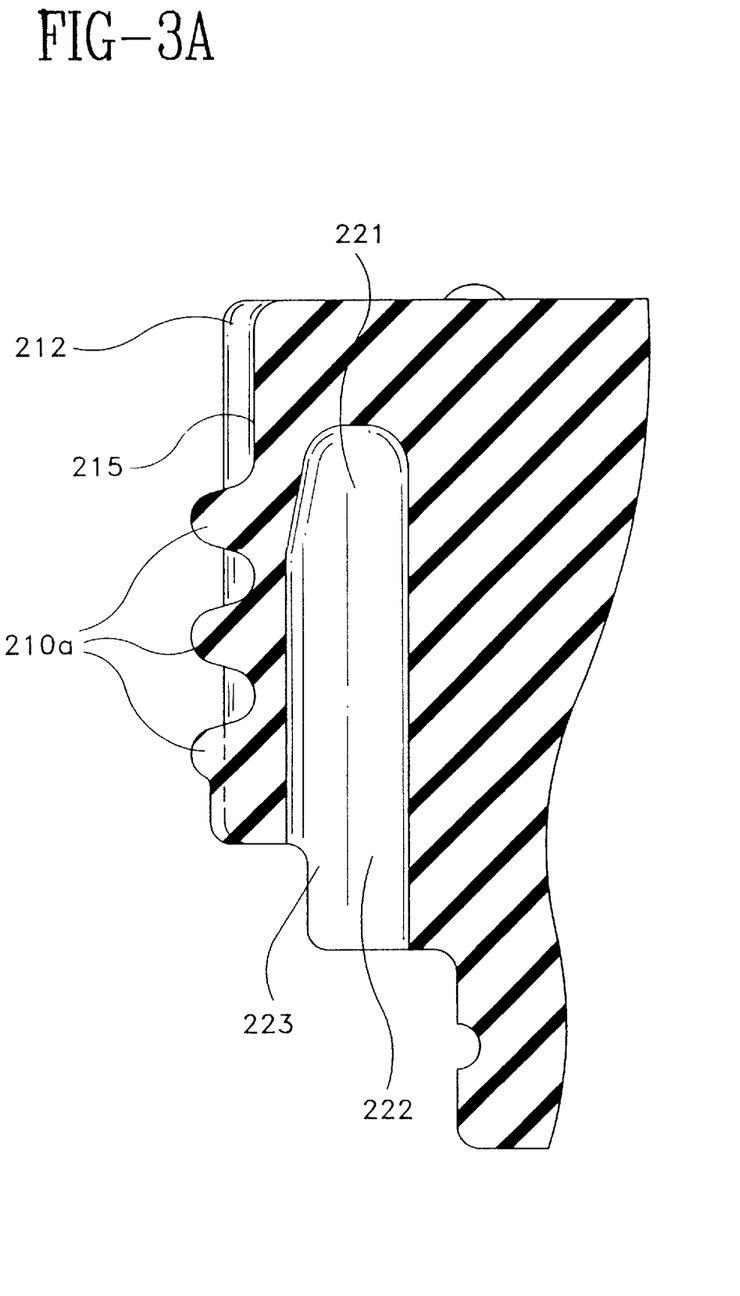
FIG. 3A depicts another way of providing a recess in the sidewall of the sequential stopper body.

One way to space a portion of cylindrical sidewall 202 from interior surface 140 of syringe barrel 100 is to provide a recess 215 in the sidewall, substantially aligned with longitudinal axis 208, in an area located between longitudinal sealing elements 212 and adjacent proximal end 204 (see FIG. 3A). In the embodiment of the stopper assembly depicted in FIGS. 1–3, the sidewall is spaced from the interior surface of the syringe barrel by providing a sloping surface 214 on cylindrical sidewall 202, adjacent proximal end 204 of the stopper, in an area between the longitudinal sealing elements. Sloping surface 214 extends obliquely outwardly on cylindrical sidewall 202 from proximal end 204 to the proximal-most of circumferential sealing elements 210a. The governing consideration is that a portion of the sidewall be spaced from the interior surface of the syringe barrel in order that fluid have access to that area of the sidewall. It will be noted that because of the presence of recess 215 or sloping surface 214, circumferential sealing element 210b is only partially circumferentially disposed about the sequential stopper body such that it does not extend between longitudinal sealing elements 212.

A further feature of the stopper assembly 200 in accordance with the present invention, is that it prevents the accumulation of fluid between distal end 228 of flow channelizer 225 and internal shoulder 302 associated with syringe barrel 100 (see FIGS. 6–12). To this end, flow channelizer 225 features a distally directed, conically-shaped projection 230 on distal end 228. While here depicted as a conus, it will be realized that conically-shaped projection 230 can assume any shape generally approaching a conus. Conically-shaped projection 230 is characterized by a base 236 intersecting with distal end 228 of the flow channelizer, and features a peaked tip 234 and a wall portion 235 extending between the peaked tip and the base. It will be noted that the shape and dimensions of distally directed, conically-shaped projection 230 are preferably shaped to conform to the shape assumed by distal shoulder 302 in a manner to minimize any dead space between them which would otherwise trap fluid.

It will be appreciated by the skilled artisan that it may be difficult to control the shape or dimensions associated with certain portions of syringe barrel 100. For instance, one area particularly difficult to control is the shape of the bottom of the syringe barrel such as at internal shoulder 302. Accordingly, if desired, structure can be incorporated on conically-shaped projection 230 to account for any tolerance or shape differences at distal shoulder 302. Referring to FIG. 2, conically-shaped projection 230 can optionally feature one or more discontinuities, such as one or more raised ribs 250 which act to prevent immediate sealing of fluid passage 108 in the area of internal shoulder 302. Accordingly, any liquid trapped in the dead space between distal shoulder 302 and conically-shaped projection 230 can run along raised ribs 250 through fluid passage 108 for delivery by needle cannula 400 attached to distal tip 104 of syringe barrel 200 (see FIGS. 6–12). The raised ribs can be designed so as to tend to collapse at the end of the injection phase, permitting substantially full surface contact between wall portion 235 of the conical projection and distal shoulder 302 of the syringe barrel to insure that nothing remains trapped between them. It will be understood by the skilled artisan that grooves may be employed in lieu of, or in combination with, ribs 250.

Turning now to FIGS. 6–12, operation of stopper assembly 200 in conjunction with multi-chambered syringe barrel 100 will now be explained. Syringe barrel 100 features an open proximal end 102, a closed distal end 104, and a substantially cylindrical chamber wall 106 extending therebetween. Distal shoulder 302 is located adjacent closed distal end 104. Syringe barrel 100 (more specifically chamber wall 106) includes the aforementioned interior surface 140 that defines a fluid-receiving compartment within the syringe barrel. Stopper assembly 200 is preferably located within syringe barrel 100 at a location intermediate proximal and distal ends 102, 104, such as to define a chamber 130 distally of flow channelizer 225 that contains a quantity of lyophilized medicament "M" intended to be reconstituted. A cannula assembly 400 may be attached in a conventional manner to distal end 104 of the syringe barrel such that it is in communication with syringe passage 108. It will be realized that if desired, various sealing means may be incorporated in passage 108 and/or with needle cannula 400 to isolate medicament "M" until such time as injection is desired.

Proximally of sequential stopper body 201, syringe barrel 100 is separated into one or more separate chambers, each capable of holding disparate components in isolation until such time as an injection sequence begins. In the embodiment depicted herein, the portion of syringe barrel 100 located proximally of sequential stopper body 201 is separated into two chambers 132, 134 by a dividing by-pass stopper 120. Bypass stopper 120 includes a proximal end 122, a distal end 121 and may be of conventional construction for sliding, fluid-tight relation with interior surface 140 of the syringe barrel. Chamber 132 may contain a diluent "D" which will be used to reconstitute lyophilized medicament "M", while chamber 134 may contain a flush agent "F" which will help remove substantially all of reconstituted medicament ("M+D") from the syringe barrel so that it can be delivered through passage 108. As will be evident to the skilled artisan, by suitably configuring the dimensions of the syringe barrel and its components, as well as the location of by-pass 110 on the syringe barrel (see below), the portion of syringe barrel 100 located proximally of sequential stopper body 201 can be divided into as many separate chambers as desired, and consequently holding the the desired number of disparate substances, by employing an appropriate number of by-pass stoppers 120.

In order to exert force during the injection phase, a plunger stopper 114 is located within syringe barrel 100 in sliding fluid-tight relation with interior surface 140. A plunger rod 116 may be threadably connected to plunger stopper 114, with a thumb plate 118 provided at the other end of plunger rod 116. A flange 107 can be formed around open proximal end 102 of the syringe barrel to enable digital manipulation of the syringe barrel during use.

Syringe barrel 100 features a by-pass 110 in cylindrical sidewall 106 of the syringe barrel. By-pass 110 defines a fluid by-pass channel 112. Fluid by-pass channel 112 provides a break in what would otherwise be complete fluid-tight contact between circumferential sealing elements 210a, b of the sequential stopper body (as well as sealing elements associated with bypass stopper 120) and interior surface 140 of the syringe barrel as stopper assembly 200 and bypass stopper 120 are urged in the distal direction towards shoulder 302. Fluid bypass channel 112 permits the passage of fluid held proximally of the sequential stopper body into the medicament chamber 130 via the fluid flow channels 238 established within a fluid channelizer 225.

As will become more evident hereinbelow, the dimensions of the various components and their placement within syringe barrel 100 is such that by-pass channel 112 serves as a fluid conduit for all of fluid held proximally of sequential stopper body 201 apart from the proximal-most of the fluids held within the syringe barrel. Here, the proximal-most of the fluids is denoted by flush agent "F" located within chamber 134. At such time as all of the fluids, apart from the proximal-most of the fluids, has been urged into medicament chamber 130 and out passage 108, the proximal-most of the retained fluids will be located in the syringe barrel at a point distal of by-pass channel 112. At this point, fluid pressure will be exerted upon sloping surface 214 of sequential stopper body 201 to open fluid conduit 310, as hereinafter described.

Figure 6:
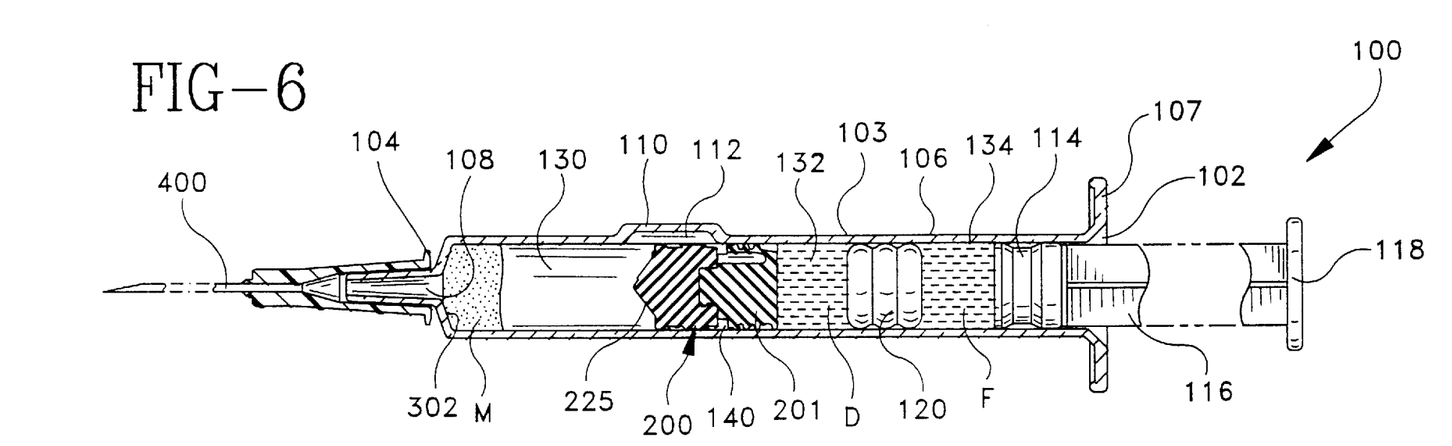
FIG. 6 is a cross-sectional view of the syringe assembly of FIG. 1 before beginning an injection sequence, illustrating the syringe assembly holding medicament in its lyophilized form as well as disparate contents held in separate chambers.

Explaining now the sequence of an injection employing a stopper assembly 200 in accordance with the present invention, in FIG. 6, syringe 100 includes a charge of lyophilized medicament "M" in chamber 130. A charge of a diluent "D" is located in a chamber 132 defined within syringe barrel 100. A charge of flush agent "F" is located in a chamber 134, delimited from chamber 132 via by-pass stopper 120. Plunger stopper 114 is located at the proximal limit of chamber 134.

Figure 7:
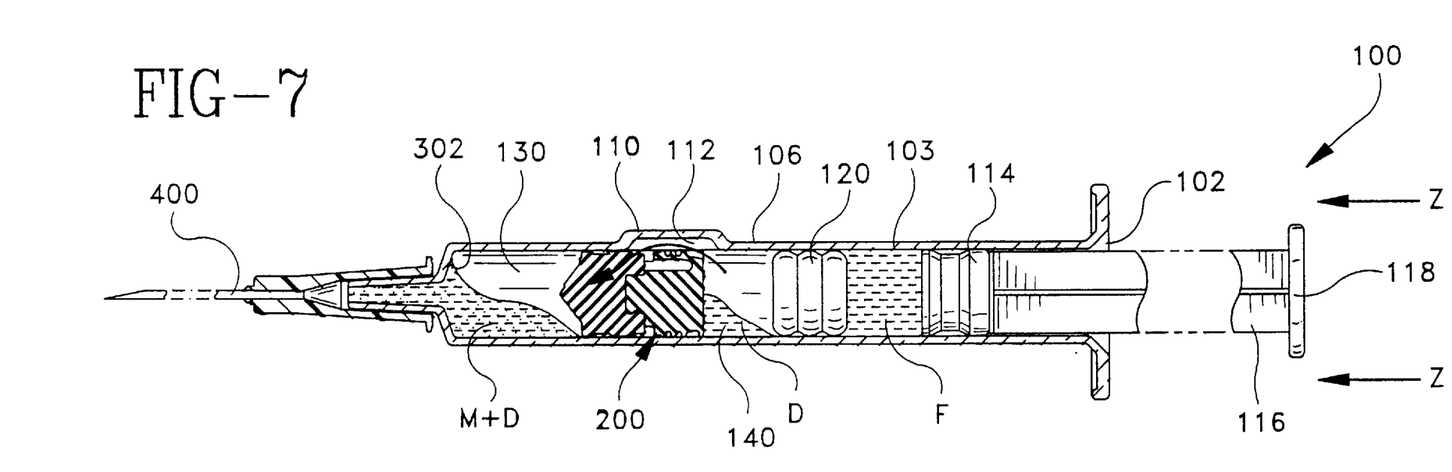
FIG. 7 is a second cross-sectional view of the syringe assembly of FIG. 1, illustrating the delivery of a diluent from one of the separate chambers through the bypass channel of the syringe barrel and the fluid flow channel of the flow channelizer to reconstitute the lyophilized medicament during an injection sequence.

In FIG. 7, a user has begun an injection sequence by beginning to move plunger rod 116 in the direction "Z". The force exerted by the user upon plunger rod 116 causes plunger stopper 114 to move flush agent "F", by-pass stopper 120, diluent "D" and stopper assembly 200 in a distal direction. At some stage of the injection sequence, circumferential sealing elements 210 will encounter by-pass channel 112. This will open by-pass channel 112 to diluent "D", allowing diluent "D" to pass through by-pass channel 112 and pass through fluid flow channels 238 of the flow channelizer to enter the medicament chamber 130. The helical arrangement of fluid flow channels 238 causes a swirling action of the diluent "D" entering within medicament chamber 130. The swirling of diluent "D" promotes full reconstitution of the charge of medicament "M". As soon as all of diluent "D" has been transferred into medicament chamber 230, proximal end 204 of the sequential stopper body and distal end 121 of the bypass stopper will be in contact. At this point, owing to continuing, distally directed force on the bypass stopper, stopper assembly 200 will move distally to commence injection of the reconstituted medicament "M+D".

Figure 8:
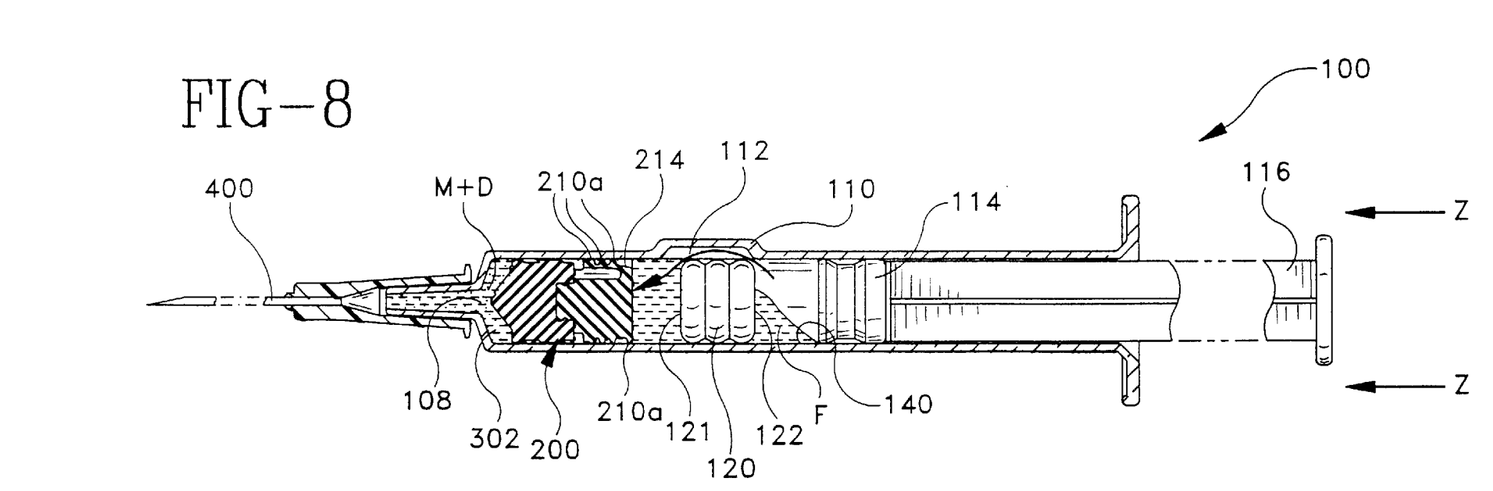
FIG. 8 is a third cross-sectional view of the syringe assembly of FIG. 1, illustrating the delivery of the now-reconstituted medicament from the passage of the syringe barrel and the distal movement of a flush agent from its chamber into the adjacent chamber formerly occupied by the diluent.

FIG. 8 illustrates a user's continued exertion of plunger rod 116 in direction Z. It will be noted that stopper assembly 200 has passed completely distally of by-pass channel 112, while proximal end 122 of by-pass stopper 120 has passed just distally of the onset of by-pass channel 112. At this point, reconstituted medicament "M+D" in chamber 230 continues to be delivered through passage 108 of syringe barrel 100. At the same time, flush agent "F" passes from chamber 134 through by-pass channel 112 to enter chamber 132 that formerly contained diluent "D".

FIG. 9 illustrates continued injection of reconstituted medicament "M+D". Flow channelizer 225 is not yet seated against distal internal shoulder 302 of the syringe barrel. Continued distal motion "Z" of plunger rod 116 has forced all of flush agent "F" into chamber 132, such that proximal end 122 of the by-pass stopper and plunger stopper 114 are now in contact.

FIG. 10 illustrates substantial completion of the injection phase involving reconstituted medicament "M+D". It will be seen that flow channelizer 225 is now seated adjacent distal shoulder 302 of the syringe barrel. Force continues to be urged upon plunger stopper 114/by-pass stopper 120, pushing the charge of flush agent "F" against sequential stopper body 201. It will be noted that at this point, the dimensions of the various components are such that stopper assembly 200 is located distally of bypass channel 112, such that circumferential sealing elements 210 of the sequential stopper body are in full contact with interior surface 140 of the syringe barrel. In order to expel flush agent "F", it is necessary to create fluid conduit 310 within sequential stopper body 201.

Referring to FIGS. 2–5 and 10–12, after conically-shaped projection 230 is seated adjacent internal shoulder 302 of syringe barrel 100, continued fluid force exerted upon proximal end 204 of the sequential stopper body will be directed to the area of sloping surface 214. The absence of circumferential sealing element 210b between longitudinal sealing elements 212 causes fluid (here, flush agent "F") to exert force upon sloping surface 214. It will be noted that circumferential sealing elements 210 (particularly proximal-most circumferential sealing element 210b) and longitudinal sealing elements 212 remain in sealing contact with interior surface 140 of the syringe barrel, in a manner to prevent fluid from being directed between interior surface 140 of the syringe barrel and cylindrical sidewall 202 of the sequential stopper body.

The continued fluid force exerted by flush agent "F" upon sloping surface 214 causes the sloping surface to collapse towards elongated hollowed chamber 220. Collapse of sloping surface 214 towards the hollowed chamber urges collapse of the portion of sidewall 202 between the longitudinal sealing elements. Particularly, sections 210c of circumferential sealing elements 210a (sections 210c are the portions of circumferential sealing elements 210a disposed between longitudinal sealing elements 212) will also separate from contact with the interior surface 140 of syringe barrel 100. By insuring that longitudinal sealing elements 212 are separated a sufficient distance "Y" with respect to maximum width "W" of chamber 220, longitudinal sealing elements 212 will themselves remain of substantial fluid-tight contact with interior surface 140 of the syringe barrel. As seen in FIGS. 10–12, the effect of the collapse of sloping surface 114 and separation of sections 210c from interior surface 140 of the syringe barrel is to create a fluid conduit 210 between the proximal and distal ends 204, 206 of the sequential stopper body. Fluid conduit 310 is substantially restricted to an area of sidewall 202 defined between longitudinal sealing elements 212. Flush agent "F" located proximally of sequential stopper body 201 will thus pass through fluid conduit 310 and enter fluid flow channels 238 of flow channelizer 225. Flush agent "F" will pass distally of channelizer 225 for delivery through passage 108. Flush agent "F" serves to remove the residual reconstituted medicament "M+D" remaining in chamber 130, such that the reconstituted medicament is substantially fully delivered to the patient. Flush agent "F" located proximally of sequential stopper body 201 can only pass distally of the sequential stopper body via fluid conduit 310. By preventing the accumulation of fluid between cylindrical sidewall 202 of the sequential stopper body and interior surface 140 of the syringe barrel, and by substantially eliminating dead space between distal shoulder 302 of the syringe barrel and distal end 228 of the flow channelizer, and by providing a single fluid conduit 310 between the proximal and distal end of the sequential stopper body, substantially all of the fluid held proximally of the stopper assembly directed distally through a passage 208 delivery by piercing element 400.

The longitudinal and circumferential sealing elements of sequential stopper body 210 can be made from the same material forming the sequential stopper body. The sequential stopper body 201 and flow channelizer 225 are preferably formed from suitable elastomeric materials, such as rubbers or thermoplastic elastomers or other materials known to the skilled artisan that are suitable for forming syringe stoppers. The same will be true of by-pass stopper 120 and plunger stopper 114. The various stoppers and their associated components can be formed to suitable dimensions to accommodate various sizes of syringes encountered in practice. It will also be appreciated by the skilled artisan that various lubricating treatments, such as siliconizing treatments, various coating treatments such as spraying treatments, or various filming treatments such as PTFE filming treatments, can be applied to any of the stoppers to improve sliding performance within the syringe barrel as need or desire dictate.

It will be appreciated and understood by those skilled in the art that further and additional forms of the invention may be devised without departing from the spirit and scope of the appended claims, the invention not being limited to the specific embodiments shown.

We claim:

1. A stopper assembly enabling reconstitution of a dry medicament held in a syringe barrel and enabling substantially complete sequential delivery of disparate contents separately held in the syringe barrel, comprising:

a sequential stopper body responsive to fluid forces for enabling the sequential delivery of said disparate contents separately held in chambers of the syringe barrel that are distal and proximal to the sequential stopper body, said sequential stopper body having a generally cylindrical sidewall with a distal end, a proximal end, and a longitudinal axis therethrough; and a generally cylindrical flow channelizer mounted to the distal end of the sequential stopper body to enable reconstitution of the dry medicament held in the syringe barrel distally of said flow channelizer, said flow channelizer having opposed proximal and distal ends and a generally cylindrical outer surface extending therebetween, at least one fluid flow channel extending between said proximal and distal ends of said flow channelizer, and a distally directed, conically-shaped projection located on the distal end of the flow channelizer.

2. The stopper assembly of claim 1, wherein said sequential stopper body and said flow channelizer are formed as a unitary component.

3. The stopper assembly of claim 1, wherein said sequential stopper body and said flow channelizer include cooperative structure such that said sequential stopper body is attached to said flow channelizer.

4. The stopper assembly of claim 3, wherein said cooperative structure comprises adhesively bonding said flow channelizer to said sequential stopper body.

5. The stopper assembly of claim 3, wherein said cooperative structure comprises at least one aperture in the proximal end of said flow channelizer and at least one projection in the distal end of said sequential stopper body, said projection mated to said aperture to mount said flow channelizer to said sequential stopper body.

6. The stopper assembly of claim 5, wherein said projection and said aperture comprise at least one groove element and at least one hub element complementary to said groove element such that said flow channelizer and said sequential stopper body are substantially fixedly mated to one another.

7. The stopper assembly of claim 3, wherein said projection is releasably mated to said aperture.

8. The stopper assembly of claim 7, wherein said projection and said aperture comprise complementary threads such that said flow channelizer is releasably mated to said sequential stopper body.

9. The stopper assembly of claim 1, wherein said at least one fluid flow channel includes a plurality of fluid flow channels.

10. The stopper assembly of claim 9, wherein plurality of fluid flow channels are helically oriented around said flow channelizer from said distal end thereof to said proximal end thereof.

11. The stopper assembly of claim 1, wherein said sequential stopper body further comprises:
- an elongate hollow chamber disposed within said sequential stopper body, said hollow chamber having a distal end, a proximal end and a width;
- at least one circumferential sealing element circumferentially disposed about the cylindrical sidewall of the sequential stopper body for sealing engagement with the inside surface of the syringe barrel;
- a pair of longitudinal sealing elements longitudinally disposed along the sidewall of the sequential stopper body in parallel relation to the longitudinal axis for sealing engagement with the inside surface of the syringe barrel, said pair of longitudinal sealing elements separated along the sidewall by a distance at least equal to the width of the hollow chamber; and
- a recessed surface provided on the cylindrical sidewall of the sequential stopper body, said recessed surface located adjacent the proximal end of the sequential stopper body and between the pair of longitudinal sealing elements;
- wherein in response to fluid pressure exerted upon the proximal end of the sequential stopper body, said recessed surface will allow the portion of sidewall located between the pair of longitudinal sealing elements to collapse towards said hollow chamber, said longitudinal sealing elements themselves remaining in fluid tight contact with the syringe barrel, to provide a fluid conduit between the proximal and distal ends of the sequential stopper body limited to that portion of the sidewall between the longitudinal sealing elements to direct substantially all of the fluid held proximally of the sequential stopper body towards said at least one fluid channel of said flow channelizer.

12. The stopper assembly of claim 11, wherein said recessed surface comprises a sloping surface.

13. The stopper assembly according to claim 1, wherein said at least one circumferential sealing element comprises a proximal circumferential sealing element disposed adjacent the proximal end of the sequential stopper body.

14. The stopper assembly according to claim 13, wherein said proximal circumferential sealing element is partially circumferentially disposed about said stopper body.

15. The stopper assembly according to claim 1, wherein said plurality of circumferential sealing elements comprise ribs.

16. The stopper assembly of claim 1, wherein said distally directed conically-shaped projection comprises a tip, a base located adjacent the distal end of the stopper body and a wall portion extending therebetween.

17. The stopper assembly of claim 16, wherein said distally-directed conically-shaped projection further comprises one or more discontinuities on the wall portion.

18. The stopper assembly of claim 17, wherein said one or more discontinuities comprises one or more ribs.

19. The stopper assembly of claim 17, wherein said one or more discontinuities comprises one or more grooves.

20. The stopper assembly of claim 1, wherein said stopper assembly is formed of an elastomeric material.

21. The stopper assembly of claim 20, wherein said elastomeric material is selected from the group consisting of rubbers or thermoplastic elastomers.

* * * * *